US011311331B2

(12) United States Patent
Akagane et al.

(10) Patent No.: US 11,311,331 B2
(45) Date of Patent: Apr. 26, 2022

(54) THERMAL TREATMENT SYSTEM

(71) Applicant: Olympus Corporation, Hachioji (JP)

(72) Inventors: Tsunetaka Akagane, Hachioji (JP); Yuto Miyauchi, Kokubunji (JP)

(73) Assignee: OLYMPUS CORPORATION, Tokyo (JP)

(*) Notice: Subject to any disclaimer, the term of this patent is extended or adjusted under 35 U.S.C. 154(b) by 299 days.

(21) Appl. No.: 16/584,055

(22) Filed: Sep. 26, 2019

(65) Prior Publication Data
US 2020/0015884 A1 Jan. 16, 2020

Related U.S. Application Data

(63) Continuation of application No. PCT/JP2017/013968, filed on Apr. 3, 2017.

(51) Int. Cl.
A61B 18/14 (2006.01)
A61B 18/10 (2006.01)

(52) U.S. Cl.
CPC .......... *A61B 18/1482* (2013.01); *A61B 18/10* (2013.01); *A61B 2018/142* (2013.01); *A61B 2018/144* (2013.01)

(58) Field of Classification Search
CPC ................ A61B 18/1482; A61B 18/10; A61B 2018/142; A61B 2018/144;
(Continued)

(56) References Cited

U.S. PATENT DOCUMENTS

2013/0138102 A1* 5/2013 Twomey ............ A61B 18/1445
606/45
2014/0185251 A1* 7/2014 Enomoto .................. G09F 3/00
361/749

(Continued)

FOREIGN PATENT DOCUMENTS

JP 2004-329764 11/2004
JP 2014-144183 8/2014

(Continued)

OTHER PUBLICATIONS

International Search Report and Written Opinion from corresponding International Application No. PCT/JP2017/013968, dated Jun. 20, 2017.

*Primary Examiner* — Linda C Dvorak
*Assistant Examiner* — Mystee Nguyen Delgado
(74) *Attorney, Agent, or Firm* — Oliff PLC

(57) ABSTRACT

A treatment system includes an energy source apparatus and a thermal treatment tool configured to receive electrical energy from the energy source apparatus. The thermal treatment tool includes a thermally conductive member having opposed respective treatment and installation surfaces. A board being disposed on the installation surface and having respective longitudinal and widthwise directions. The board includes an electrically conductive wire having a conductive portion and a heat generating portion for generating heat when supplied with electric energy. The board is folded back at a folded point and is disposed on the thermally conductive member such that the heat generating portion of the electrically conductive wire facing the installation surface.

22 Claims, 6 Drawing Sheets

(58) Field of Classification Search
CPC ........ A61B 2017/2925; A61B 18/1442; A61B 18/1445; A61B 2017/2926; A61B 17/28; A61B 17/29; A61B 2017/320094; A61B 2017/320078; A61B 2018/1455; A61B 2017/320095; A61M 25/0067
See application file for complete search history.

(56) References Cited

U.S. PATENT DOCUMENTS

| | | | |
|---|---|---|---|
| 2015/0327909 A1 | 11/2015 | Nakamura | |
| 2015/0335375 A1 | 11/2015 | Nakamura | |
| 2015/0373829 A1* | 12/2015 | Ishikawa | H05K 3/4691 |
| | | | 174/254 |
| 2016/0295336 A1* | 10/2016 | Moller | H04R 25/65 |
| 2016/0324566 A1 | 11/2016 | Kudo | |
| 2017/0014175 A1 | 1/2017 | Takashino et al. | |
| 2017/0042614 A1* | 2/2017 | Salahieh | A61B 18/1206 |
| 2017/0215941 A1* | 8/2017 | Kazuno | A61B 18/085 |

FOREIGN PATENT DOCUMENTS

| | | |
|---|---|---|
| JP | 2015-208415 | 11/2015 |
| WO | 2014119391 | 8/2014 |
| WO | 2015111662 | 7/2015 |
| WO | 2016035471 | 3/2016 |

\* cited by examiner

THERMAL TREATMENT SYSTEM

CROSS-REFERENCE TO RELATED APPLICATION

This application is a continuation application of PCT Application No. PCT/JP 2017/013968 filed on Apr. 3, 2017, which is hereby incorporated by reference in its entirety.

TECHNICAL FIELD

The disclosed technology relates generally to a thermal treatment system, and more particularly, some embodiments relate to a thermal treatment tool that performs a treatment using heat generated by a heat generating body.

DESCRIPTION OF THE RELATED ART

US 2015/0327909 A1 discloses a treatment tool having a pair of grippers capable of gripping a treatment target such as a biotissue or the like between the pair of grippers. One of the grippers includes a thermally conductive member that is electrically conductive and thermally conductive. The thermally conductive member includes a treatment surface facing the other gripper. The thermally conductive member also includes an installation surface facing away from the treatment surface. A board is attached to the installation surface by an adhesive sheet that is electrically insulative and thermally conductive. A heat generating wire, or an electrically conductive wire, that generates heat when supplied with electric energy is disposed on a front surface of the board. The board is mounted on the thermally conductive member such that the front surface of the board faces the side of the board on which the thermally conductive member is positioned. Heat generated by the heat generating wire is transferred to the treatment surface through the adhesive sheet and the thermally conductive member, and then applied from the treatment surface to the treatment target that is gripped between the grippers. The other gripper includes an electrically conductive member. When electric energy is supplied to the thermally conductive member of the one gripper and the electrically conductive member of the other gripper, a high-frequency current flows between the thermally conductive member and the electrically conductive member through the gripped treatment target.

In the treatment tool disclosed in US Patent Application Pub. No. 2015/0327909 A1, the heat generating wire has two connection terminals disposed on a proximal-end portion of the gripper. Each of the connection terminals is connected to an electric supply path in the form of an electric wire or the like. The heat generating wire has a folded point disposed on the distal-end portion of the gripper. On the board, the heat generating wire extends toward a distal-end side from one of the connection terminals to the folded point and then extends toward a proximal-end side from the folded point to the other connection terminal. Therefore, the heat generating wire is substantially U-shaped on the board, providing two electric channels extending along the longitudinal directions of the board. When electric energy is supplied to the heat generating wire, a short circuit may be caused between the two electric channels.

BRIEF SUMMARY OF EMBODIMENTS

The disclosed technology has been made in view of the foregoing.

One aspect of the disclosed technology is directed to a thermal treatment tool. The thermal treatment tool includes a thermally conductive member having opposed respective treatment and installation surfaces and a board is disposed on the installation surface and having respective longitudinal and widthwise directions. The board includes an electrically conductive wire having a conductive portion and a heat generating portion for generating heat when supplied with electric energy. The board is folded back at a folded line and is disposed on the thermally conductive member such that the heat generating portion of the electrically conductive wire facing the installation surface.

Another aspect of the disclosed technology is directed to a treatment system having an energy source apparatus and a thermal treatment tool configured to receive electrical energy from the energy source apparatus. The thermal treatment tool includes a thermally conductive member having opposed respective treatment and installation surfaces and a board being disposed on the installation surface and having respective longitudinal and widthwise directions. The board includes an electrically conductive wire having a conductive portion. A heat generating portion for generating heat when supplied with electric energy. The board is folded back at a folded line and disposed on the thermally conductive member such that the heat generating portion of the electrically conductive wire facing the installation surface.

A further aspect of the disclosed technology is directed to a treatment system having an energy source apparatus and a thermal treatment tool configured to receive electrical energy from the energy source apparatus. The thermal treatment tool includes a thermally conductive member having opposed respective treatment and installation surfaces. A board is disposed on the installation surface and having respective longitudinal and widthwise directions. A film is disposed between the thermally conductive member and the board and being thermally conductive and electrically insulative. The board includes an electrically conductive wire having a conductive portion having a cover member being impermeable and electrically insulative. A heat generating portion for generating heat when supplied with electric energy. The board is folded back at a folded line and disposed on the thermally conductive member such that the heat generating portion of the electrically conductive wire facing the installation surface.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide a thermal treatment tool that prevents a short circuit from being caused between electric channels that are provided on a board by a heat generating wire.

First Embodiment

Figure 1:
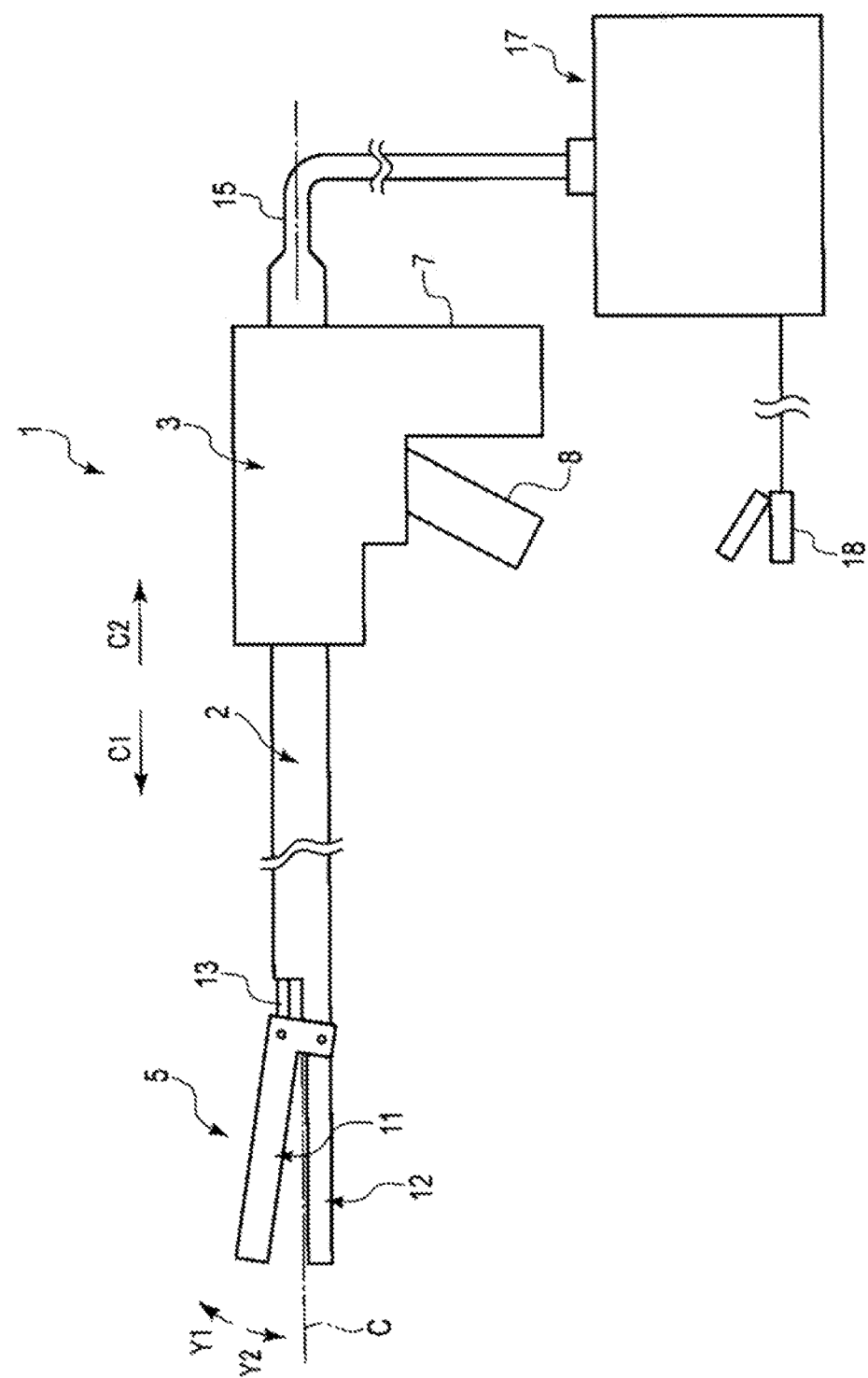
FIG. 1 is a schematic view illustrating a treatment system incorporating a treatment tool according to a first embodiment.

A first embodiment of the disclosed technology will be described below with reference to FIGS. 1 through 5. FIG. 1 is a schematic view illustrating a treatment system incorporating a treatment tool 1 as a thermal treatment tool according to the present embodiment. As illustrated in FIG. 1, the treatment tool 1 includes a shaft 2, a housing 3, and an end effector 5, or gripping unit. The shaft 2 has a longitudinal axis C as a central axis thereof and extends along the longitudinal axis C. One side in a direction along the longitudinal axis C will be referred to as a distal-end side, i.e., a direction C1 side, whereas the opposite side to the distal-end side as a proximal-end side, e.g., a direction C2 side. The housing 3 is coupled to the proximal-end side of the shaft 2. The end effector 5 is disposed on the distal-end portion of the shaft 2.

The housing 3 includes a grip 7 extending in a direction across the longitudinal axis C. A handle 8 is angularly movably attached to the housing 3. When the handle 8 is angularly moved with respect to the housing 3, the handle 8 is opened or closed with respect to the grip 7. According to the example illustrated in FIG. 1, the handle 8 is positioned on the side of the longitudinal axis C where the grip 7 is positioned, and is positioned on the distal-end side of the grip 7. When the handle 8 is opened and closed, the handle 8 moves substantially parallel to the longitudinal axis C. According to an example, however, the handle 8 is positioned on the proximal-end side of the grip 7. According to another example, the handle 8 is positioned on the side of the longitudinal axis C that is opposite to the side where the grip 7 is positioned, and when the handle 8 is opened and closed, the handle 8 moves across, i.e., substantially perpendicularly to, the longitudinal axis C. According to an example, an operating member (not illustrated) such as a rotary knob or the like, is mounted on the housing 3. When the rotary knob is rotated about the longitudinal axis C, the shaft 2 and the end effector 5 rotate together about the longitudinal axis C with respect to the housing 3.

The end effector 5 includes a pair of grippers 11 and 12, or jaws. According to an example, one of the grippers 11 and 12 is integrally formed with or fixed to the shaft 2, whereas the other of the grippers 11 and 12 is angularly movably attached to the shaft 2. For example, according to the example illustrated in FIG. 1, the gripper 11 is angularly movably attached to the shaft 2, whereas the gripper 12 is fixed to the shaft 2. According to another example, both the grippers 11 and 12 are angularly movably attached to the shaft 2. The shaft 2 houses therein a movable member 13 extending from the proximal-end side to distal-end side thereof, and has a distal-end portion connected to the end effector 5. The movable member 13 has a proximal-end portion coupled to the handle 8 in the housing 3. When the handle 8 is opened or closed with respect to the grip 7, the movable member 13 moves along the longitudinal axis C. At least one of the grippers 11 and 12 is thus angularly moved with respect to the shaft 2, opening or closing the space between the grippers 11 and 12. Since the space between the grippers 11 and 12 is openable and closable, a treatment target such as a biotissue or the like can be gripped between the grippers 11 and 12. Directions in which the end effector 5 is opened and closed, respectively, i.e., directions indicated by the arrow Y1 and the arrow Y2, extend across, i.e., substantially perpendicularly to, the longitudinal axis C.

A cable 15 has an end connected to the housing 3 of the treatment tool 1. The other end of the cable 15 is connected to an energy source device 17 separate from the treatment tool 1. The system that incorporates the treatment tool 1 includes an operating member 18. According to the example illustrated in FIG. 1, the operating member 18 is a foot switch separate from the treatment tool 1 and is electrically connected to the energy source device 17. Based on an operation made on the operating member 18, the energy source device 17 supplies electric energy to the treatment tool 1. Because of the electric energy supplied from the energy source device 17 to the treatment tool 1, a treatment energy is applied to the treatment target gripped between the grippers 11 and 12 in a manner to be described hereinafter. According to an example, as the operating member 18, an operating button or the like mounted on the housing 3 is mounted on the housing 3 instead of or in addition to the foot switch.

Figure 2:
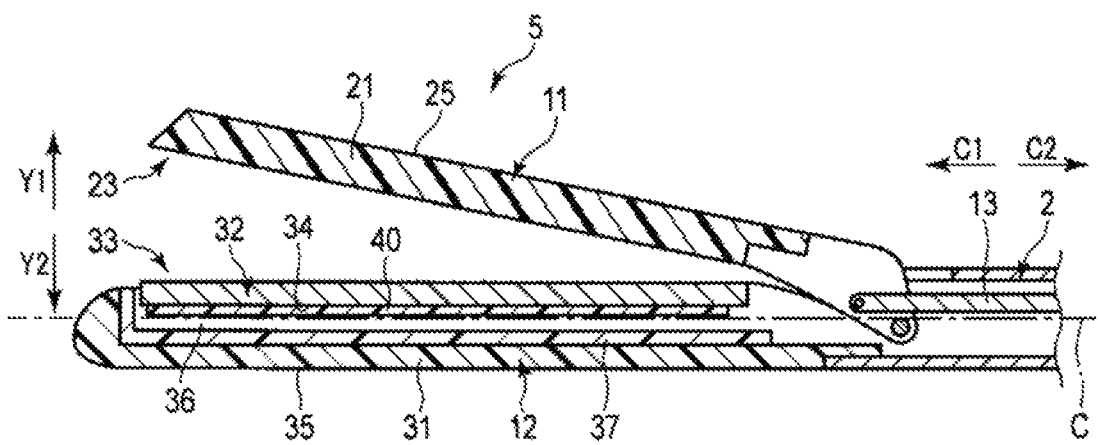
FIG. 2 is a schematic view illustrating a cross section of an end effector according to the first embodiment, taken substantially perpendicularly to the widthwise directions thereof.
Figure 3:
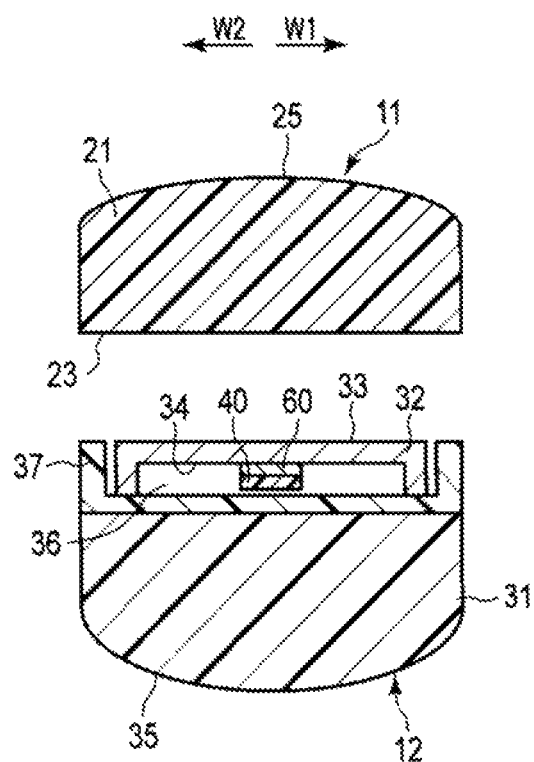
FIG. 3 is a schematic view illustrating a cross section of the end effector according to the first embodiment, taken substantially perpendicularly to the longitudinal directions thereof.

FIGS. 2 and 3 are views illustrating the make-up of the end effector 5. There are defined herein widthwise directions, i.e., directions indicated by the arrow W1 and the arrow W2, of the end effector 5, extending across, i.e., substantially perpendicularly to, directions along the longitudinal axis C and also across, i.e., substantially perpendicularly to, the directions in which the end effector 5 is opened and closed, respectively. FIG. 2 illustrates a cross section of the end effector 5, taken substantially perpendicularly to the widthwise directions thereof. FIG. 3 illustrates a cross section of the end effector 5, taken substantially perpendicularly to the directions along the longitudinal axis C.

As illustrated in FIGS. 2 and 3, the gripper 11 includes a support body 21 attached to the shaft 2. The support body 21 extends in a range from the proximal-end portion to distal-end portion of the gripper 11 in the directions along the longitudinal axis C. The gripper 11 also includes a facing surface 23 facing the gripper 12 and a rear surface 25 facing away from the facing surface 23. According to the present embodiment, the facing surface 23 and the rear surface 25 are defined by the support body 21.

The gripper 12 includes a support body 31 attached to the shaft 2, a support member 37, or blade support, attached to the support body 31, and a thermally conductive member 32, or blade, attached to the support member 37. Each of the support body 31, the support member 37, and the thermally conductive member 32 extends in a range from the proximal-end portion to distal-end portion of the gripper 12 in the directions along the longitudinal axis C. The support body 31 and the support member 37 should preferably be made of a material that is electrically insulative and has a low thermal conductivity. For example, the support member 37 is made of a resin material such as PEEK, i.e., polyetheretherketone, liquid crystal polymer, or the like.

The support member 37 is attached to the side of the support body 31 where the gripper 11 is positioned. The thermally conductive member 32, or blade, is attached to the support member 37. The thermally conductive member 32 is attached to the side of the support member 37 where the gripper 11 is positioned. The thermally conductive member 32 is made of metal such as aluminum alloy or the like or a material that is highly thermally conductive. The gripper 12 includes a treatment surface 33, or facing surface, facing the facing surface 23 of the gripper 11 and a rear surface 35 facing away from the treatment surface 33. According to the present embodiment, the rear surface 35 is defined by the support body 31, and the treatment surface 33 is defined by the thermally conductive member 32.

The gripper 12 has a cavity 36 defined therein that is surrounded by the thermally conductive member 32 and the support member 37. The cavity 36 is defined in a range from the proximal-end portion to distal-end portion of the gripper 12 in the directions along the longitudinal axis C. The thermally conductive member 32 is disposed adjacent to the cavity 36 on a side where the treatment surface 33 is positioned and both sides in the widthwise directions of the end effector 5. The support member 37 is disposed adjacent to the cavity 36 on the distal-end side thereof and a side where the rear surface 35 is positioned.

According to the example illustrated in FIGS. 2 and 3, the facing surface 23 of the gripper 11 and the treatment surface 33 of the gripper 12 extend substantially parallel to the widthwise directions of the end effector 5. According to an example, however, the facing surface 23 of the gripper 11 has a central portion in the widthwise directions that is made concave toward the rear surface 25, and the treatment surface 33 of the gripper 12 has a central portion in the widthwise directions that is made convex toward the gripper 11. According to another example, the facing surface 23 of the gripper 11 has a central portion in the widthwise directions that is made convex toward the gripper 12, and the treatment surface 33 of the gripper 12 has a central portion in the widthwise directions that is made concave toward the rear surface 35.

The thermally conductive member 32 has an installation surface 34 facing away from the treatment surface 33. The installation surface 34 faces the side where the support body 31 is positioned in the gripper 12, and is disposed adjacent to the cavity 36. A heat generating module 40, or sheet heater, is disposed in the cavity 36. As illustrated in FIG. 3, the heat generating module 40 is bonded to the installation surface 34 through an adhesive sheet 60, or film. The heat generating module 40 and the adhesive sheet 60 extend in a range from the proximal-end portion to distal-end portion of the gripper 12 in the directions along the longitudinal axis C. The adhesive sheet 60 is made of a material that has an adhesive function, is electrically insulative, and is highly thermally conductive, i.e., has a small thermal resistance. For example, the adhesive sheet 60 is made of a mixture of epoxy resin and ceramics.

Figure 4:
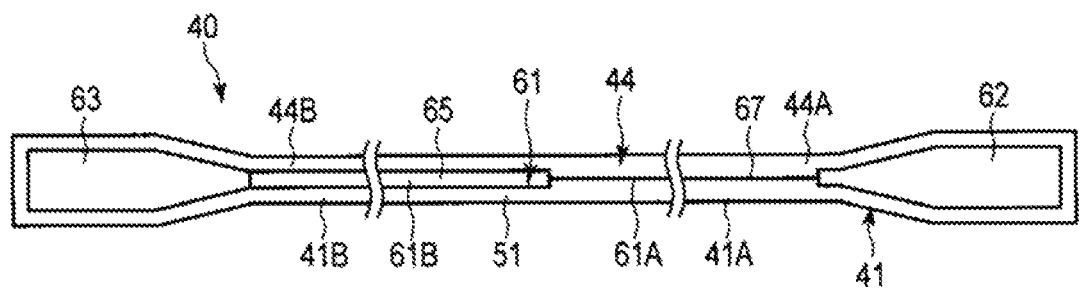
FIG. 4 is a schematic view illustrating a heat generating module according to the first embodiment before it is attached to a thermally conductive member.
Figure 5:
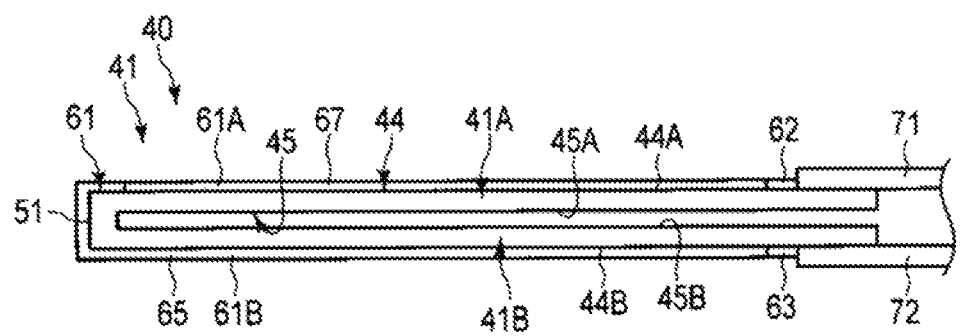
FIG. 5 is a schematic view illustrating the heat generating module according to the first embodiment, as viewed from one of the widthwise directions of the end effector.

FIGS. 4 and 5 are views illustrating the make-up of the heat generating module 40. FIG. 4 is a view illustrating the heat generating module 40 before it is attached to the thermally conductive member 32. FIG. 5 is a view illustrating the heat generating module 40 attached to the thermally conductive member 32, as viewed from one of the widthwise directions of the gripper 12, i.e., the end effector 5.

As illustrated in FIG. 4, the heat generating module 40, or sheet heater, includes a board 41 and an electrically conductive wire 61 disposed on the board 41. The board 41 is low in thermal conductivity and is electrically insulative. The board 41 is, for example, a flexible board made of a resin such as polyimide or the like. The board 41 is a flat plate having longitudinal directions and widthwise directions. The board 41 is of a strip shape that is longer in the longitudinal directions than in the widthwise directions. The electrically conductive wire 61 extends in a range from one end to other end of the board 41 in the longitudinal directions thereof. The electrically conductive wire 61 is electrically conductive. The electrically conductive wire 61 is, for example, a metal film made of nichrome alloy, stainless alloy, or the like.

The heat generating module 40 has a folded point 51 in the longitudinal directions. The folded point 51 should preferably be positioned centrally in the longitudinal directions of the heat generating module 40. The board 41 includes a first portion 41A and a second portion 41B that are disposed respectively on both sides of the folded point 51 in the longitudinal directions of the board 41. The first portion 41A extends from the folded point 51 toward one end of the board 41, and the second portion 41B extends from the folded point 51 toward the other end of the board 41. The board 41 is folded back or bent at the folded point 51, and attached to the installation surface 34 of the thermally conductive member 32 such that the first portion 41A and the second portion 41B lie one over the other.

The board 41 includes a front board surface 44 on which the electrically conductive wire 61 is disposed and a rear board surface 45 facing away from the front board surface 44. The front board surface 44 faces in one of the thicknesswise directions of the board 41, whereas the rear board surface 45 faces in the other of the thicknesswise directions of the board 41. The first portion 41A includes a front surface portion 44A serving as part of the front board surface 44 and a rear surface portion 45A serving as part of the rear board surface 45. The second portion 41B includes a front surface portion 44B serving as part of the front board surface 44 and a rear surface portion 45B serving as part of the rear board surface 45.

The electrically conductive wire 61 is disposed on the front board surface 44. The electrically conductive wire 61 extends substantially parallel to the longitudinal directions of the board 41. The electrically conductive wire 61 includes two connection terminals 62 and 63, or connecting portions. The connection terminal 62 is disposed on the front surface portion 44A of the board 41. An electric supply path 71 in the form of an electric wire or the like has an end connected to the connection terminal 62. The electric supply path 71 extends through the shaft 2, the housing 3, and the cable 15, and has its other end connected to the energy source device 17. The connection terminal 63 is disposed on the front surface portion 44B of the board 41. An electric supply path 72 in the form of an electric wire or the like has an end connected to the connection terminal 63. The electric supply path 72 extends through the shaft 2, the housing 3, and the cable 15, and has its other end connected to the energy source device 17. Therefore, the energy source device 17, the electric supply path 71, the electrically conductive wire 61, and the electric supply path 72 make up an electric channel for supplying electric energy to the electrically conductive wire 61 of the treatment tool 1.

The electrically conductive wire 61 includes a first electrically conductive portion 61A disposed on the front surface portion 44A of the first portion 41A and a second electrically conductive portion 61B disposed on the front surface portion 44B of the second portion 41B. The first electrically conductive portion 61A extends along the longitudinal directions of the board 41 from the connection terminal 62 to the folded point 51. The second electrically conductive portion 61B extends along the longitudinal directions of the board 41 from the folded point 51 to the connection terminal 63. The folded point 51 is positioned between the first electrically conductive portion 61A and the second electrically conductive portion 61B in the longitudinal directions of the board 41.

The electrically conductive wire 61 includes a non-heat generating portion 65, or conductive portion, and a heat generating portion 67. The non-heat generating portion 65 extends from the connection terminal 63 toward the connection terminal 62 between the connection terminals 62 and 63. The heat generating portion 67 is disposed between the non-heat generating portion 65 and the connection terminal 62. The heat generating portion 67 extends from the connection terminal 62 toward the connection terminal 63 up to the non-heat generating portion 65.

The heat generating portion 67 is a heat generating wire attached to the board 41 or a heat generating pattern or the like printed on the board 41. When electric energy is supplied to the electrically conductive wire 61, the heat generating portion 67 generates heat due to electric resistance thereof. The heat generating portion 67 is of a curved shape having a wavy meandering pattern. In this case, the electrically conductive wire 61 extends over an increased length in the heat generating portion 67 and the portion of the board 41 on which heat generating portion 67 is disposed has an increased area, compared with a heat generating portion that is of a straight shape. Therefore, the amount of heat generated by the heat generating portion 67 is increased. The heat generating portion 67 is made of, for example, nichrome alloy, stainless alloy, or the like. Stainless alloy has a large temperature coefficient of resistance compared with nichrome alloy or the like. Consequently, in a case where the heat generating portion 67 is made of stainless alloy, it is easy to control the temperature at which the heat generating portion 67 generates heat, using the resistance value of an electric circuit including the heat generating portion 67, compared with a heat generating portion made of nichrome alloy or the like.

The non-heat generating portion 65 has a larger width in the widthwise directions than the heat generating portion 67. The electrically conductive wire 61 of the non-heat generating portion 65 has a larger cross-sectional area perpendicular to the longitudinal directions than the heat generating portion 67. Therefore, the non-heat generating portion 65 has a high mechanical strength and a small electrical resistance compared with the heat generating portion 67. As a result, the non-heat generating portion 65 generates almost no heat even when the electrically conductive wire 61 is supplied with electric energy.

According to the present embodiment, the heat generating portion 67 is disposed within the range of the front surface portion 44A of the first portion 41A. Consequently, of the electrically conductive wire 61, the non-heat generating portion 65 that is mechanically stronger than the heat generating portion 67 is disposed at the folded point 51.

As illustrated in FIG. 5, when the heat generating module 40 is to be attached to the thermally conductive member 32, the board 41 is folded back or bent at the folded point 51, making the first portion 41A and the second portion 41B lie one over the other. With the board 41 folded back at the folded point 51, causing the front surface portion 44A of the first portion 41A of the board 41 to face the installation surface 34 of the thermally conductive member 32, the heat generating module 40 is attached to the installation surface 34 of the thermally conductive member 32. On the board 41, the first portion 41A extends from the proximal-end portion of the gripper 12 toward the distal-end side thereof and is folded back at the folded point 51 positioned at the distal-end portion of the gripper 12, and the second portion 41B extends from the folded point 51 toward the proximal-end side on the rear surface 35 side of the first portion 41A. On the board 41, therefore, the first portion 41A is attached to the installation surface 34 of the thermally conductive member 32, and the second portion 41B is disposed on the rear surface 35 side of the first portion 41A.

With the heat generating module 40 attached to the thermally conductive member 32, the thicknesswise directions of the board 41 extend substantially parallel to the directions in which the grippers 11 and 12 are opened and closed, and the widthwise directions of the board 41 extend substantially parallel to the widthwise directions of the gripper 12 and the end effector 5. The longitudinal directions of the board 41 extend substantially parallel to the longitudinal axis C of the shaft 2. The folded point 51 is positioned at the distal-end portion of the installation surface 34 of the thermally conductive member 32. The connection terminals 62 and 63 of the electrically conductive wire 61 are disposed on the proximal-end portion of the gripper 12.

The first portion 41A of the board 41 is attached to the installation surface 34 of the thermally conductive member 32 through the adhesive sheet 60. The front surface portion 44A of the first portion 41A faces the installation surface 34. The rear surface portion 45A of the first portion 41A faces away from the front surface portion 44A, i.e., faces the rear surface 35.

The second portion 41B of the board 41 is disposed to lie under the first portion 41A on the rear surface 35 side. The rear surface portion 45B of the second portion 41B faces the rear surface portion 45A of the first portion 41A. The front surface portion 44B of the second portion 41B faces away from the rear surface portion 45B. The front surface portion 44B faces the rear surface 35 side and is exposed in the cavity 36. The front surface portion 44B faces away from the front surface portion 44A. Therefore, the connection terminal 62 disposed on the front surface portion 44A and the connection terminal 63 disposed on the front surface portion 44B face away from each other.

Based on an operation made on the operating member 18, the energy source device 17 supplies a direct current or an alternating current as electric energy to the electrically conductive wire 61. When the direct current or the alternating current flows through the electrically conductive wire 61, the heat generating portion 67 generates heat. At this time, the non-heat generating portion 65 generates almost no heat even though it is supplied with the electric energy. The heat generated by the heat generating portion 67 is transferred through the adhesive sheet 60 to the thermally conductive member 32. Since the adhesive sheet 60 is highly thermally conductive, i.e., has a small thermal resistance, the heat generated by the heat generating portion 67 is efficiently transferred to the thermally conductive member 32.

The electrically conductive wire 61 is disposed on the front surface portion 44A and the front surface portion 44B of the front board surface 44. According to the present embodiment, a single electric channel made of the electrically conductive wire 61 and extending substantially parallel to the longitudinal axis C and the longitudinal directions of the board 41 is disposed on each of the front surface portion 44A and the front surface portion 44B of the front board surface 44.

The first portion 41A and the second portion 41B of the board 41 that are electrically insulative exist between the first electrically conductive portion 61A disposed on the front surface portion 44A of the first portion 41A of the board 41 and the second electrically conductive portion 61B disposed on the front surface portion 44B of the second portion 41B of the board 41 in the thicknesswise directions of the board 41. Therefore, the first electrically conductive portion 61A disposed on the front surface portion 44A and the second electrically conductive portion 61B disposed on the front surface portion 44B are electrically insulated from each other in the thicknesswise directions of the board 41.

The non-heat generating portion 65 of the electrically conductive wire 61 is disposed at the folded point 51. Therefore, the electrically conductive wire 61 is folded back or bent in the non-heat generating portion 65. Since the non-heat generating portion 65 is folded back, its strength at the time its material is elongated is higher than the heat generating portion 67. Therefore, the non-heat generating portion 65 is less likely to break than the heat generating portion 67 when it is folded back.

Next, operation and advantages of the treatment tool 1 according to the present embodiment will be described below. For performing a treatment using the treatment tool 1, the surgeon holds the housing 3 of the treatment tool 1 and inserts the end effector 5 into a body cavity such as an abdominal cavity or the like. A treatment target such as a blood vessel or the like is placed between the grippers 11 and 12, and the handle 8 is closed on the grip 7, thereby closing the space between the grippers 11 and 12. The grippers 11 and 12 now grip a biotissue such as a blood vessel or the like therebetween as the treatment target.

With the treatment target gripped between the grippers 11 and 12, an operation is entered through the operating member 18 to supply electric energy from the energy source device 17 to the electrically conductive wire 61. When the electric energy is supplied to the electrically conductive wire 61, the heat generating portion 67 of the electrically conductive wire 61 generates heat. The heat generated by the heat generating portion 67 is transferred through the adhesive sheet 60 to the thermally conductive member 32. The thermally conductive member 32 is made of a material that is highly thermally conductive. Therefore, the heat transferred from the electrically conductive wire 61 is transferred to the thermally conductive member 32 in its entirety. The heat transferred to the thermally conductive member 32 is applied from the treatment surface 33 to the treatment target. The heat is now applied as a treatment energy to the treatment target gripped between the grippers 11 and 12, coagulating or incising the treatment target. In this manner, the treatment surface 33 carries out a treatment to apply heat to the gripped treatment target.

According to the present embodiment, the board 41 is folded back at the folded point 51 and attached to the thermally conductive member 32 such that the first portion 41A and the second portion 41B lie one over the other. The board 41 that is electrically insulative exists between the first electrically conductive portion 61A and the second electrically conductive portion 61B of the electrically conductive wire 61 in the thicknesswise directions of the board 41. Therefore, the first electrically conductive portion 61A and the second electrically conductive portion 61B are electrically insulated from each other by the board 41 that is electrically insulative. As the first electrically conductive portion 61A and the second electrically conductive portion 61B are electrically insulated from each other, a short circuit is effectively prevented from being caused between the first electrically conductive portion 61A and the second electrically conductive portion 61B.

According to the thermal treatment tool disclosed in US 2015/0327909 A1, the two electric channels that extend on the board 41 from the folded point 51 toward the proximal-end side are spaced from each other in the widthwise directions of the board 41, and are disposed on the front board surface 44. In this case, the distance between the two electric channels needs to be kept sufficiently for preventing a short circuit from being caused therebetween. Therefore, the dimension of the board 41 in the widthwise directions cannot be reduced.

On the other hand, according to the present embodiment, the single electric channel that extends along the longitudinal directions of the board 41 is disposed on the front board surface 44 of the board 41. Furthermore, the two electric channels 61A and 61B that extend on the board 41 from the folded point 51 toward the proximal-end side are spaced from each other in the thicknesswise directions of the board 41. Therefore, the electric channels do not need to be juxtaposed in the widthwise directions, allowing the board 41 to have a reduced dimension in the widthwise directions of the board 41. Thus, the heat generating module 40 can be reduced in size in the widthwise directions thereof.

According to the present embodiment, furthermore, the non-heat generating portion 65 of the electrically conductive wire 61 is disposed at the folded point 51. Therefore, with the board 41 folded back at the folded point 51, the electrically conductive wire 61 is folded back in the non-heat generating portion 65. The non-heat generating portion 65 is less likely to break than the heat generating portion 67 when it is folded back. Consequently, the electrically conductive wire 61 maintains its durability compared with an electrically conductive wire 61 folded back in the heat generating portion 67.

Figure 6:
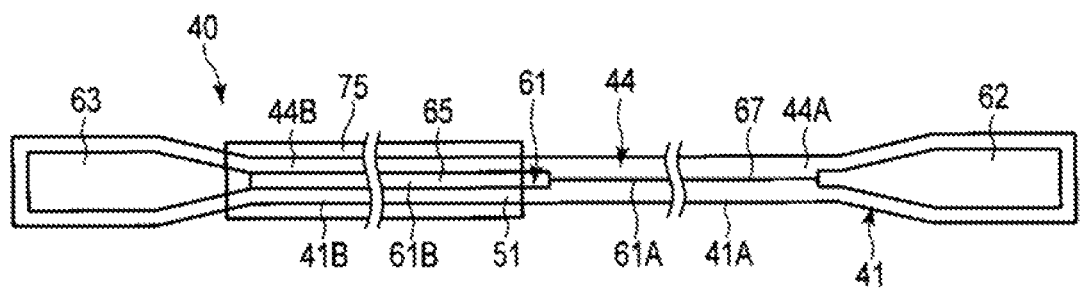
FIG. 6 is a schematic view illustrating a heat generating module according to an example of the first embodiment before it is attached to the thermally conductive member.

According to an example, as illustrated in FIG. 6, the front surface portion 44B of the second portion 41B of the board 41 should preferably include a cover member 75 that covers the second electrically conductive portion 61B of the electrically conductive wire 61. The cover member 75 is made of, for example, a cover lay, a sealing material, a melted polyimide layer, or the like. The cover member 75 that is water-resistance and covers the second electrically conductive portion 61B increases water tightness of the second electrically conductive portion 61B. The cover member 75 that is electrically insulative and covers the second electrically conductive portion 61B is effective to prevent a short circuit from being caused between the first electrically conductive portion 61A and the second electrically conductive portion 61B through water or the like that may be brought into contact with the heat generating module 40.

The heat generating portion 67 is disposed on only the front surface portion 44A of the first portion 41A of the front board surface 44 of the board 41. Therefore, the electrically conductive wire 61 generates heat only from its portion attached to the thermally conductive member 32. Thus, the heat generated by the heat generating portion 67 is efficiently transferred to the thermally conductive member 32. The heat generating portion 67 is not disposed on the front surface portion 44B of the second portion 41B. Consequently, the heat generated by the heat generating portion 67 is prevented from being transferred to the rear surface 35 side through the cavity 36.

First Modification of the First Embodiment

Figure 7:
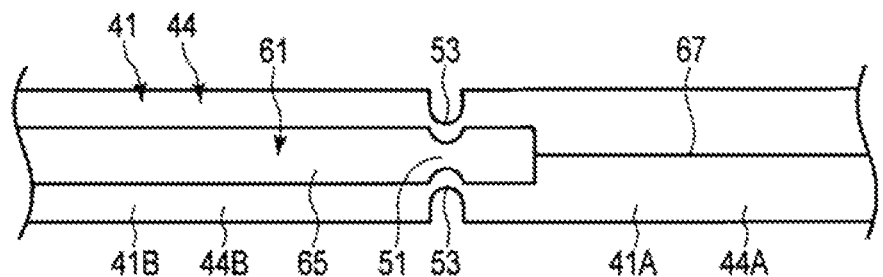
FIG. 7 is a schematic view illustrating a heat generating module according to a first modification of the first embodiment.

FIG. 7 is a schematic view illustrating a heat generating module 40 according to a first modification of the first embodiment. According to the present modification, a pair of recesses 53 are defined in edges of the board 41 at the folded point 51 of the heat generating module 40. The recesses 53 are defined respectively in the edges of the board 41 in the widthwise directions thereof. The recesses 53 face each other in the widthwise directions of the board 41. The recesses 53 make the both sides of the board 41 concave in the widthwise directions thereof. At the folded point 51, therefore, the width of the board 41 is smaller than the width of the portion of the board 41 other than the folded point 51. The recesses 53 at the folded point 51 of the heat generating module 40 are effective to restrain repulsive forces, or spring-back forces, produced when the board 41 is folded back at the folded point 51.

Second Modification of the First Embodiment

Figure 8:
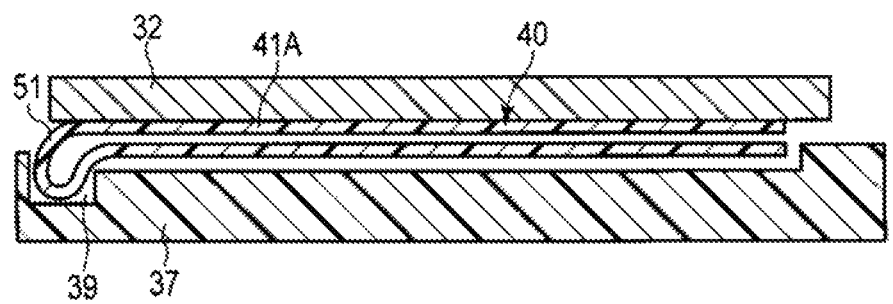
FIG. 8 is a schematic view illustrating a cross section of a heat generating module and a holding member according to a second modification of the first embodiment, taken substantially perpendicularly to the widthwise directions thereof.

FIG. 8 is a schematic view illustrating the thermally conductive member 32, the heat generating module 40, and the support member 37 according to a second modification of the first embodiment. According to the present modification, the support member 37 includes a groove 39, or concavity, extending toward the rear surface 35 side. The groove 39 is defined in the distal-end portion of the support member 37. When the thermally conductive member 32 to which the heat generating module 40 is attached is disposed on the support member 37, the folded point 51 of the heat generating module 40 is positioned at the groove 39.

In the vicinity of the folded point 51 of the heat generating module 40, the dimension of the board 41 in the widthwise directions increases when the board 41 is folded back and bulges. According to the present modification, since the groove 39 is defined in the portion of the support member 37 near the folded point 51 of the heat generating module 40, the thermally conductive member 32 and the heat generating module 40 are effectively attached to the support member 37.

It is also preferable for the installation surface 34 of the thermally conductive member 32 to have a groove, or concavity, defined therein where the folded point 51 of the heat generating module 40 is disposed, instead of or in addition to the groove 39 defined in the support member 37.

Second Embodiment

Figure 9:
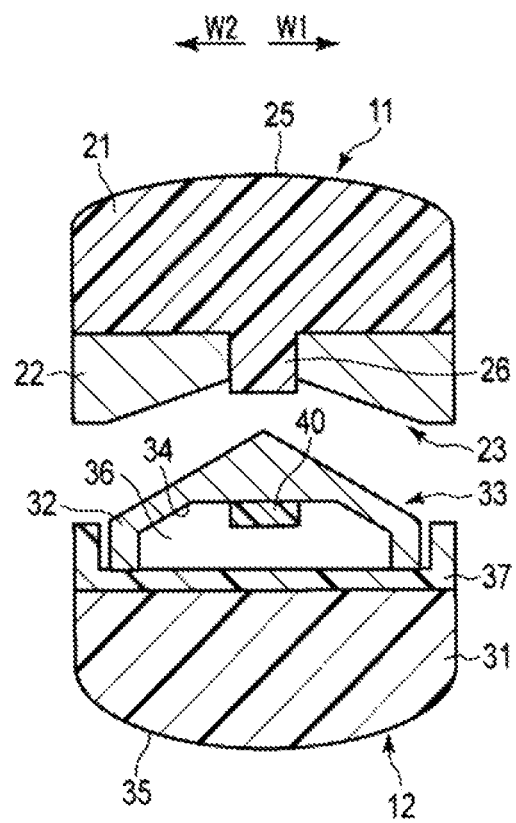
FIG. 9 is a schematic view illustrating a cross section of an end effector according to a second embodiment, taken substantially perpendicularly to the longitudinal directions thereof.

Next, a second embodiment of the disclosed technology will be described below. The second embodiment is similar to the first embodiment except that the configuration of the first embodiment is modified as described below. Those parts of the second embodiment that are identical to those of the first embodiment are denoted by identical numeral reference, and will not be described below. FIG. 9 is a schematic view illustrating the make-up of an end effector 5 according to the second embodiment. According to the present embodiment, a high-frequency energy, or high-frequency current, is used as a treatment energy, in addition to the heat generated by the heat generating portion 67 of the electrically conductive wire 61 of the heat generating module 40.

As illustrated in FIG. 9, the gripper 11 further includes an electrically conductive member 22 fixed to the support body 21. The electrically conductive member 22 is made of an electrically conductive metal or the like. The electrically conductive member 22 is attached to the side of the support body 21 where the gripper 12 is positioned. The electrically conductive member 22 extends in a range from the proximal-end portion to distal-end portion of the gripper 11 in the directions along the longitudinal axis C. According to the present embodiment, the support body 21 provides the rear surface 25, and the support body 21 and the electrically conductive member 22 provide the facing surface 23.

The support body 21 includes a protrusion 26 protruding toward the side where the gripper 12 is positioned. The protrusion 26 serves as part of the facing surface 23. The electrically conductive member 22 is disposed on both sides of the protrusion 26 in the widthwise directions of the end effector 5, i.e., in the widthwise directions of the gripper 11. An electric supply path (not illustrated) in the form of an electric wire or the like has an end connected to the electrically conductive member 22. The electric supply path extends through the shaft 2, the housing 3, and the cable 15, and has its other end connected to the energy source device 17.

According to the present embodiment, the thermally conductive member 32 is made of a material that is electrically conductive. An electric supply path (not illustrated) in the form of an electric wire or the like has an end connected to the thermally conductive member 32. The electric supply path extends through the shaft 2, the housing 3, and the cable 15, and has its other end connected to the energy source device 17.

Based on an operation made on the operating member 18, the energy source device 17 outputs high-frequency electric power as an electric energy. The high-frequency electric power that is output is supplied through the electric supply path described hereinbefore to the electrically conductive member 22 of the gripper 11 and through the electric supply path described hereinbefore to the thermally conductive member 32 of the gripper 12. The electrically conductive member 22 and the thermally conductive member 32 thus function as electrodes whose potentials are different from each other. With the treatment target gripped between the grippers 11 and 12, since the electrically conductive member 22 and the thermally conductive member 32 function as electrodes, a high-frequency current flows through the treatment target between the electrically conductive member 22 and the thermally conductive member 32 and is applied as a treatment energy to the treatment target. In other words, the high-frequency energy is applied as a treatment energy between the treatment surface 33 and the facing surface 23. The applied high-frequency current promotes coagulation of the treatment target. As described hereinbefore, the treatment surface 33 according to the present embodiment supplies a high-frequency energy, i.e., a high-frequency current, to the treatment target gripped between the grippers 11 and 12.

While the space between the grippers 11 and 12 is being closed, the thermally conductive member 32 can abut against the protrusion 26 of the support body 21 at the facing surface 23 of the gripper 11. With the thermally conductive member 32 abutting against the protrusion 26 of the support body 21, a gap is defined between the thermally conductive member 32 and the electrically conductive member 22, and the thermally conductive member 32 does not contact the electrically conductive member 22. Therefore, while the electrically conductive member 22 and the thermally conductive member 32 are functioning as electrodes, the electric energy output from the energy source device 17 to the thermally conductive member 32 and the electrically conductive member 22 is effectively prevented from causing a short circuit in the electric circuit.

According to the present embodiment, the electric energy, i.e., direct current electric power or alternating current electric power, supplied to the electrically conductive wire 61 also causes the electrically conductive wire 61 to generate heat. The heat generated by the electrically conductive wire 61 is transferred through the adhesive sheet 60 and the thermally conductive member 32 to the treatment surface 33, which applies the heat to the treatment target.

Modification of the Second Embodiment

Furthermore, according to the present embodiment, the thermally conductive member 32 and the electrically conductive member 22 function as electrodes, and a bipolar treatment is performed to cause a high-frequency current to flow through the treatment target between the thermally conductive member 32 and the electrically conductive member 22. However, the disclosed technology is not limited to such details. According to a modification of the present embodiment, for example, the gripper 11 is dispensed with, and a treatment portion having the same configuration as the gripper 12 is disposed on the distal-end portion of the shaft 2. In this case, the system that incorporates the treatment tool 1 includes a counter electrode plate (not illustrated). In a treatment, the counter electrode plate is placed outside of and attached to a human body or the like. According to the present modification, the energy source device 17 supplies high-frequency electric power to the thermally conductive member 32 and the counter electrode plate. Then, a monopolar treatment is carried out to cause a high-frequency current to flow through the treatment target between the treatment surface 33 of the thermally conductive member 32 and the counter electrode plate.

Third Embodiment

Figure 10:
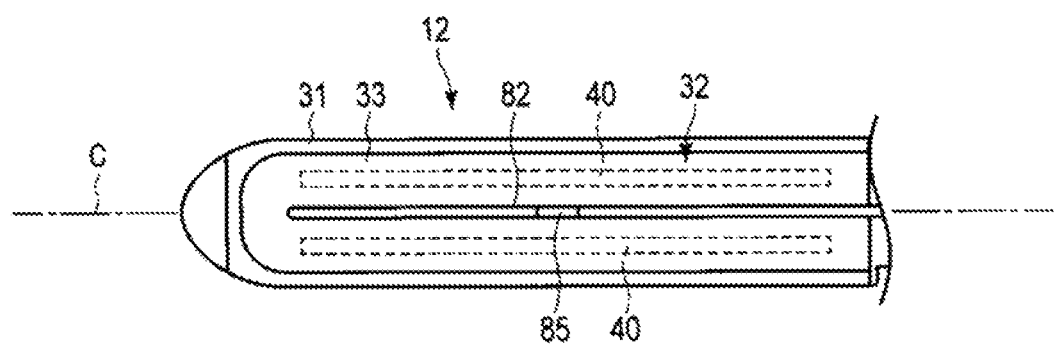
FIG. 10 is a schematic view of a gripper according to a third embodiment as viewed from a side where another gripper is positioned.
Figure 11:
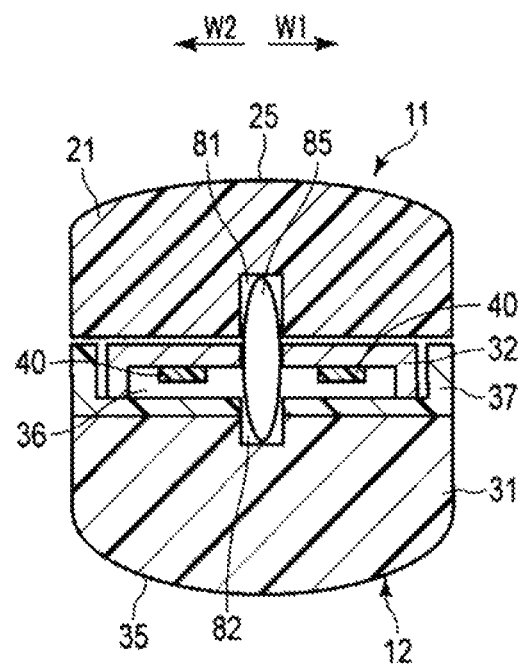
FIG. 11 is a schematic view illustrating a cross section of an end effector according to the third embodiment, taken substantially perpendicularly to the longitudinal directions thereof.

Next, a third embodiment of the disclosed technology will be described below with reference to FIGS. 10 and 11. The third embodiment is similar to the first embodiment except that the configuration of the first embodiment is modified as described below. Those parts of the third embodiment that are identical to those of the first embodiment are denoted by identical numeral reference, and will not be described below. FIG. 10 is a view of a gripper 12 according to the present embodiment as viewed from a gripper 11 side. FIG. 11 is a view illustrating a cross section of the grippers 11 and 12 according to the present embodiment, taken substantially perpendicularly to the longitudinal axis C.

According to the present embodiment, the gripper 11 includes a groove 81 that is concave from the facing surface 23 toward the rear surface 25. The groove 81 is defined centrally in the facing surface 23 in the widthwise directions of the gripper 11 and the end effector 5. The groove 81 extends in a range from the proximal-end portion to distal-end portion of the gripper 11 in the directions along the longitudinal axis C. The groove 81 is open in the facing surface 23 toward the gripper 12. Moreover, the groove 81 is open in the proximal end of the support body 21 toward the proximal-end side.

The gripper 12 includes a groove 82 that is concave from the treatment surface 33 toward the rear surface 35. The groove 82 faces the groove 81. The groove 82 is defined centrally in the treatment surface 33 in the widthwise directions of the gripper 12 and the end effector 5. The groove 82 extends in a range from the proximal-end portion to distal-end portion of the gripper 12 in the directions along the longitudinal axis C. The groove 82 is open in the treatment surface 33 toward the gripper 11. Moreover, the groove 82 is open in the proximal end of the support body 31 toward the proximal-end side.

The shaft 2 houses a cutter 85 disposed therein that extends along the longitudinal axis C. In the housing 3, the cutter 85 is coupled to an operating member (not illustrated) attached to the housing 3. When the space between the grippers 11 and 12 is closed, the cutter 85 is movable along the longitudinal axis C in the end effector 5 along the groove 81 in the gripper 11 and the groove 82 in the gripper 12. Based on an operation entered through the operating member, the cutter 85 moves along the longitudinal axis C in the shaft 2 and the end effector 5 with respect to the housing 3, the shaft 2, and the end effector 5.

When a treatment is performed using the treatment tool 1 according to the present embodiment, as is the case with the first embodiment, the heat generated by the heat generating module 40 is transferred to the thermally conductive member 32, and then applied from the treatment surface 33 to the treatment target. With the treatment target coagulated, the surgeon enters an operation through the operating member to move the cutter 85 from within the shaft 2 toward the distal-end side. The cutter 85 is inserted from within the shaft 2 into the grooves 81 and 82 in the grippers 11 and 12 from the proximal-end sides thereof. Then, the cutter 85 moves along the grooves 81 and 82 toward the distal-end side in the grippers 11 and 12. The cutter 85 then incises the treatment target coagulated between the grippers 11 and 12 along the longitudinal axis C.

In the thermally conductive member 32 of the gripper 12, heat generating modules 40 similar to the heat generating module according to the first embodiment, etc., are attached to both sides of the groove 82 that extends along the longitudinal axis C. According to the present embodiment, therefore, the two heat generating modules 40 are attached to the thermally conductive member 32. The heat generated by each of the heat generating modules 40 is transferred to the thermally conductive member 32.

Common Configuration of the Embodiments

According to the embodiments, etc., described hereinbefore, the thermal treatment tool 1 includes the thermally conductive member 32 that is thermally conductive and includes the treatment surface 33 and the installation surface 34 facing away from the treatment surface 33, the electrically conductive wire 61 that is electrically conductive and includes the two connecting portions 62, 63 and the heat generating portion 67 disposed between the two connecting portions 62, 63, for generating heat when supplied with electric energy, and the board 41 including the front board surface 44 with the electrically conductive wire 61 disposed thereon and the folded point 51, the board 41 being folded back at the folded point 51 and attached to the installation surface 34 of the thermally conductive member 32 such that the heat generating portion 67 faces a side where the thermally conductive member 32 is positioned and the connecting portions 62, 63 face away from each other.

The disclosed technology is not limited to the above embodiments. Various changes and modifications may be made without departing from the scope of the invention at the time the invention is reduced to practice. Furthermore, the embodiments may be carried out in as many suitable combinations as possible with combined advantages. Moreover, the embodiments include inventions at various stages, and various inventions can be extracted by making appropriate combinations of the disclosed a plurality of components.

In sum, one aspect of the disclosed technology is directed to a thermal treatment tool. The thermal treatment tool includes a thermally conductive member having opposed respective treatment and installation surfaces and a board is disposed on the installation surface and having respective longitudinal and widthwise directions. The board includes an electrically conductive wire having a conductive portion and a heat generating portion for generating heat when supplied with electric energy. The board is folded back at a folded line and is disposed on the thermally conductive member such that the heat generating portion of the electrically conductive wire facing the installation surface.

The conductive portion has a cross-sectional area larger than the heat generating portion. The conductive portion of the electrically conductive wire is disposed at the folded line. The conductive portion includes a cover member that is electrically insulative and/or water-tight. The board includes a pair of recesses defined therein at the folded line. The thermal treatment tool further includes a support member configured to receive the thermally conductive member and the board. The support member includes a concavity in which the folded line of the board is disposed. The thermally conductive member includes a concavity defined in the installation surface in which the folded line of the board is disposed. The thermally conductive member is an electrode when supplied with electric energy. The thermal treatment tool further includes a gripper facing the treatment surface of the thermally conductive member. The gripper capable of being openable and closable with respect to the thermally conductive member. The thermally conductive member functions as an electrode when supplied with electric energy and the gripper includes an electrically conductive member that functions as an electrode whose potential energy is different from the thermally conductive member when supplied with electric energy. The thermally conductive member and the gripper includes a groove that receives a cutter therein for movement along longitudinal directions. The thermal treatment tool further includes a film disposed between the thermally conductive member and the board and being thermally conductive and electrically insulative. The film has an adhesive function and is bonded to each of the thermally conductive member and a front surface of the board, respectively.

Another aspect of the disclosed technology is directed to a treatment system having an energy source apparatus and a thermal treatment tool configured to receive electrical energy from the energy source apparatus. The thermal treatment tool includes a thermally conductive member having opposed respective treatment and installation surfaces and a board being disposed on the installation surface and having respective longitudinal and widthwise directions. The board includes an electrically conductive wire having a conductive portion. A heat generating portion for generating heat when supplied with electric energy. The board is folded back at a folded line and disposed on the thermally conductive member such that the heat generating portion of the electrically conductive wire facing the installation surface.

A further aspect of the disclosed technology is directed to a treatment system having an energy source apparatus and a thermal treatment tool configured to receive electrical energy from the energy source apparatus. The thermal treatment tool includes a thermally conductive member having opposed respective treatment and installation surfaces. A board is disposed on the installation surface and having respective longitudinal and widthwise directions. A film is disposed between the thermally conductive member and the board and being thermally conductive and electrically insulative. The board includes an electrically conductive wire having a conductive portion having a cover member being impermeable and electrically insulative. A heat generating portion for generating heat when supplied with electric energy. The board is folded back at a folded line and disposed on the thermally conductive member such that the heat generating portion of the electrically conductive wire facing the installation surface.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A thermal treatment tool comprising:
a thermally conductive member having opposed respective treatment and installation surfaces;
a board disposed on the installation surface and having respective longitudinal and widthwise directions, the board including:
a first portion that extends from a first end of the board toward a second end of the board along the longitudinal direction of the board, and
a second portion that extends from the first portion and along the board in the longitudinal direction of the board towards the first end of the board, the first portion being located closer to the installation surface than the second portion, the second portion including a folded portion, which is folded back over the first portion to overlap along the first portion; and
an electrically conductive wire including:
a heat generating portion disposed on the first portion, the heat generating portion being configured to generate heat when supplied with electric energy, and
a conductive portion disposed on the second portion, the conductive portion being configured to supply electric power to the heat generating portion.

2. The thermal treatment tool of claim 1, wherein the conductive portion has a cross-sectional area larger than a cross-sectional area of the heat generating portion.

3. The thermal treatment tool of claim 2, wherein the conductive portion of the electrically conductive wire is disposed at a folded point, which is at an apex of the folded portion.

4. The thermal treatment tool of claim 1, wherein the conductive portion includes a cover member that is electrically insulative or water-tight.

5. The thermal treatment tool of claim 1, wherein the board includes a pair of recesses located in the folded portion.

6. The thermal treatment tool of claim 1, further comprising:
a support member configured to receive the thermally conductive member and the board, the support member including a concavity in which at least a part of the folded portion of the board is disposed.

7. The thermal treatment tool of claim 1, wherein the thermally conductive member includes a concavity defined in the installation surface in which at least a part of the folded portion of the board is disposed.

8. The thermal treatment tool of claim 1, wherein the thermally conductive member is an electrode when supplied with electric energy.

9. The thermal treatment tool of claim 1, further comprising:
a gripper facing the treatment surface of the thermally conductive member, the gripper being configured to open and close with respect to the thermally conductive member.

10. The thermal treatment tool of claim 9, wherein:
the thermally conductive member functions as an electrode when supplied with electric energy, and
the gripper includes an electrically conductive member that functions as an electrode having a potential that is different from a potential of the thermally conductive member when supplied with electric energy.

11. The thermal treatment tool of claim 9, wherein the thermally conductive member and the gripper include a groove that receives a cutter in the groove for movement along the longitudinal direction.

12. The thermal treatment tool of claim 1, further comprising:
a film disposed between the thermally conductive member and the board, the film being thermally conductive and electrically insulative.

13. The thermal treatment tool of claim 12, wherein the film has an adhesive, and the film is bonded by the adhesive to each of the thermally conductive member and a front surface of the board, respectively.

14. The thermal treatment tool of claim 1, wherein the electrically conductive wire disposed on the second portion extends across to a folded line that extends in the widthwise direction of the board, and the electrically conductive wire disposed on the second portion is spaced apart from the electrically conductive wire disposed on the first portion by both the first portion and the second portion in a thickness direction of the board, which is perpendicular to the longitudinal and the widthwise directions of the board.

15. The thermal treatment tool of claim 1, further comprising:
a first connection terminal disposed closer to the first end than the electrically conductive wire disposed on the first portion; and
a second connection terminal disposed closer to the second end than the electrically conductive wired disposed on the second portion.

16. A treatment system comprising:
an energy source apparatus; and
a thermal treatment tool configured to receive electrical energy from the energy source apparatus, the thermal treatment tool including:
a thermally conductive member having opposed respective treatment and installation surfaces, a board disposed on the installation surface, the board having respective longitudinal and widthwise directions, the board including:
  a first portion that extends from a first end of the board toward a second end of the board along the longitudinal direction of the board, and
  a second portion that extends from the first portion and along the board in the longitudinal direction of the board towards the first end of the board, the first portion being located closer to the installation surface than the second portion, the second portion including a folded portion, which is folded back over the first portion to overlap along the first portion, and
an electrically conductive wire including:
  a heat generating portion disposed on the first portion, the heat generating portion being configured to generate heat when supplied with electric energy, and
  a conductive portion disposed on the second portion, the conductive portion being configured to supply electric power to the heat generating portion.

17. The treatment system of claim 16, wherein the treatment tool includes a shaft having respective proximal and distal ends, a housing, and an end effector, each of the respective housing and the end effector is attached to the respective proximal and distal ends of the shaft.

18. The treatment system of claim 17, wherein the end effector includes a pair of grippers each of which being pivotable with respect to one another or with respect to the shaft, the pair of grippers being configured to grip a treatment target.

19. The treatment system of claim 16, further comprising a film disposed between the thermally conductive member and the board, the film being thermally conductive and electrically insulative.

20. The treatment system of claim 16, further comprising a support member configured to receive the thermally conductive member and the board, the support member including a concavity in which at least a part of the folded portion of the board is disposed.

21. The treatment system of claim 16, wherein the thermally conductive member is an electrode.

22. A treatment system comprising:
an energy source apparatus; and
a thermal treatment tool configured to receive electrical energy from the energy source apparatus, the thermal treatment tool including:
  a thermally conductive member having opposed respective treatment and installation surfaces,
  a board disposed on the installation surface, the board having respective longitudinal and widthwise directions, the board including:
    a first portion that extends from a first end of the board toward a second end of the board along the longitudinal direction of the board, and
    a second portion that extends from the first portion and along the board in the longitudinal direction of the board towards the first end of the board, the first portion being located closer to the installation surface than the second portion, the second portion including a folded portion, which is folded back over the first portion to overlap along the first portion,
  a film disposed between the thermally conductive member and the board, the film being thermally conductive and electrically insulative, and
  an electrically conductive wire including:
    a heat generating portion disposed on the first portion, the heat generating portion being configured to generate heat when supplied with electric energy, and
    a conductive portion disposed on the second portion, the conductive portion having a cover member being impermeable and electrically insulative, the conductive portion being configured to supply electric power to the heat generating portion.

* * * * *